（12）United States Patent
Bruekers et al.

(10) Patent No.: US 10,758,179 B2
(45) Date of Patent: Sep. 1, 2020

(54) STRESS-MEASURING SYSTEM

(71) Applicant: KONINKLIJKE PHILIPS N.V., Eindhoven (NL)

(72) Inventors: Alphons Antonius Maria Lambertus Bruekers, Nederweert (NL); Murtaza Bulut, Eindhoven (NL); Vojkan Mihajlovic, Eindhoven (NL); Martin Ouwerkerk, Culemborg (NL); Joanne Henriette Desiree Monique Westerink, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 81 days.

(21) Appl. No.: 14/435,182

(22) PCT Filed: Oct. 16, 2013

(86) PCT No.: PCT/IB2013/059396
§ 371 (c)(1),
(2) Date: Apr. 13, 2015

(87) PCT Pub. No.: WO2014/064580
PCT Pub. Date: May 1, 2014

(65) Prior Publication Data
US 2015/0265212 A1 Sep. 24, 2015

Related U.S. Application Data

(60) Provisional application No. 61/717,186, filed on Oct. 23, 2012.

(51) Int. Cl.
*A61B 5/00* (2006.01)
*A61B 5/0205* (2006.01)
(Continued)

(52) U.S. Cl.
CPC .............. *A61B 5/4884* (2013.01); *A61B 5/02* (2013.01); *A61B 5/0205* (2013.01);
(Continued)

(58) Field of Classification Search
CPC ..... A61B 5/4884; A61B 5/7275; A61B 5/742; A61B 5/6892; A61B 5/02416;
(Continued)

(56) References Cited

U.S. PATENT DOCUMENTS 6,138,865 A * 10/2000 Gilmore ................ A61J 7/0084
221/2
6,468,234 B1 * 10/2002 Van der Loos .......... A61B 5/01
128/920

(Continued)

FOREIGN PATENT DOCUMENTS

| CN | 1773563 A | 5/2006 |
|---|---|---|
| CN | 102483610 A | 5/2012 |

(Continued)

OTHER PUBLICATIONS

Schwarzer, Ralf, and Suhair Hallum. "Perceived teacher self—efficacy as a predictor of job stress and burnout: Mediation analyses." Applied psychology 57.s1 (2008): 152-171. doi: 10.1111/j.1464-0597.2008.00359.x.*

(Continued)

Primary Examiner — Jonathan T Kuo

(57) ABSTRACT

The present invention relates to a stress-measuring system for determining a level of stress of a user, in particular for monitoring an upcoming burnout, the system (10) comprising: an alarm clock (12) for initiating an alarm at an arbitrary preset time, wherein the system (10) comprises an interface (14) for switching off the alarm; a vital sign sensor (16) for measuring a first vital sign of the user while the user operates the interface (14); and a processing unit (18) for determining (Continued)

the level of stress of the user based on the sensed first vital sign.

16 Claims, 4 Drawing Sheets

(51) Int. Cl.
| | |
|---|---|
| *A61B 5/024* | (2006.01) |
| *A61B 5/11* | (2006.01) |
| *A61B 5/1172* | (2016.01) |
| *A61B 5/02* | (2006.01) |
| *A61B 5/0402* | (2006.01) |
| *A61B 5/0408* | (2006.01) |

(52) U.S. Cl.
CPC ........ *A61B 5/02416* (2013.01); *A61B 5/0402* (2013.01); *A61B 5/0408* (2013.01); *A61B 5/1118* (2013.01); *A61B 5/1172* (2013.01); *A61B 5/486* (2013.01); *A61B 5/4809* (2013.01); *A61B 5/4812* (2013.01); *A61B 5/6843* (2013.01); *A61B 5/6892* (2013.01); *A61B 5/6898* (2013.01); *A61B 5/7275* (2013.01); *A61B 5/742* (2013.01); *A61B 5/7405* (2013.01); *A61B 5/7455* (2013.01); *A61B 2560/029* (2013.01); *A61B 2560/0468* (2013.01); *A61B 2560/0475* (2013.01); *A61B 2562/0247* (2013.01); *A61B 2562/08* (2013.01)

(58) Field of Classification Search
CPC ... A61B 5/1172; A61B 5/0205; A61B 5/6898; A61B 5/7405; A61B 5/02; A61B 5/0402; A61B 2560/0468; A61B 2560/029; A61M 2021/0027; A61M 2021/0083; G04G 13/02; G08B 21/00–0211
USPC ............... 600/301; 340/539.11–539.12, 540, 340/573.1–573.7; 702/19, 189–194; 703/11; 705/2–3
See application file for complete search history.

(56) References Cited

U.S. PATENT DOCUMENTS

| | | | | |
|---|---|---|---|---|
| 6,607,484 | B2* | 8/2003 | Suzuki | A61B 5/0002 128/903 |
| 7,117,031 | B2* | 10/2006 | Lohman | A61B 5/046 600/508 |
| 7,330,752 | B2* | 2/2008 | Kettunen | A61B 5/024 600/508 |
| 7,370,378 | B2* | 5/2008 | Nakasato | A47G 9/10 5/636 |
| 8,568,330 | B2* | 10/2013 | Mollicone | A61B 5/024 600/508 |
| 9,814,420 | B2* | 11/2017 | Badenes | A61B 5/165 |
| 9,949,681 | B2* | 4/2018 | Badenes | A61B 5/165 |
| 2001/0049471 | A1* | 12/2001 | Suzuki | A61B 5/0002 600/300 |
| 2004/0117212 | A1* | 6/2004 | Kong | G06Q 50/22 705/2 |
| 2005/0256414 | A1* | 11/2005 | Kettunen | A61B 5/024 600/509 |
| 2006/0097884 | A1 | 5/2006 | Jang et al. | |
| 2006/0213012 | A1* | 9/2006 | Nakasato | A47G 9/10 5/636 |
| 2007/0100666 | A1* | 5/2007 | Stivoric | F24F 11/30 705/3 |
| 2008/0027337 | A1* | 1/2008 | Dugan | A61B 5/0002 600/508 |
| 2009/0203998 | A1* | 8/2009 | Klinghult | A61B 5/02416 600/443 |
| 2010/0324427 | A1 | 12/2010 | Devot et al. | |
| 2012/0116176 | A1 | 5/2012 | Moravec et al. | |
| 2012/0163136 | A1 | 6/2012 | Du et al. | |
| 2012/0232414 | A1* | 9/2012 | Mollicone | A61B 5/024 600/508 |
| 2013/0013208 | A1* | 1/2013 | Ohnemus | G06F 19/3431 702/3 |
| 2017/0258384 | A1* | 9/2017 | Badenes | H04L 51/02 |
| 2017/0303841 | A1* | 10/2017 | Badenes | H04L 67/22 |

FOREIGN PATENT DOCUMENTS

| | | |
|---|---|---|
| EP | 0215548 A1 | 3/1987 |
| EP | 1163878 A1 | 12/2001 |
| EP | 1407713 A1 | 4/2004 |
| EP | 1545309 B1 | 6/2005 |
| JP | S62111690 A | 5/1987 |
| JP | 2004138439 A | 5/2004 |
| JP | 2005177306 A | 7/2005 |
| JP | 2006109895 A | 4/2006 |
| JP | 2008183205 A | 8/2008 |
| JP | 2011517982 A | 6/2011 |
| WO | 2006100676 A2 | 8/2006 |
| WO | 2009057033 A2 | 5/2009 |
| WO | 2009128000 A1 | 10/2009 |
| WO | 2011027266 A1 | 3/2011 |

OTHER PUBLICATIONS

Allen: "Photoplethsmography and Its Applicatio in Clinical Physiological Measurement"; PHYSIOL. MEAS. 28 (2007), pp. R1-R39.
Boneva et al : "Higher Heart Rate and Reduced Heart Rate Variability Persist During Sleep in Chronic Fatigue Syndrome: A Population-Based Study"; Autonomic Neuroscience:Basic & Clinical, 2007, vol. 137, pp. 94-101.
De Vente et al: "Physiological Differences Between Burnout Patients and Healthy Controls:Blood Pressure, Heart Rate, and Cortisol Responses"; Occup Environ Med 2003, vol. 60 (Suppl 1), pp. i54-i61.
Ekstedt et al: "Disturbed Sleep and Fatigue in Occupational Burnout"; Scan J Work Environ Health, 2006, vol. 32 (2), pp. 121-131.
McEwen: "Protective and Damaging Effects of Stress Mediators"; New England Journal of Medicine, vol. 338, No. 3, pp. 171-179.
McEwen: "Central Effects of Stress Hormones in Health and Disease: Understanding the Protective and Damaging Effects of Stress and Stress Mediators"; European Journal of Pharmacology, 2008, vol. 583, pp. 174-185.
Van Eekelen et al: "Circadian Variation in Base Rate Measures of Cardiac Autonomic Activity"; EUR J. APP. PHYSIOL, 2004, vol. 93. pp. 39-46.
Verkruysse et al: "Remote Plethysmographic Imaging Using Ambient Light"; Opt Express, Dec. 2008, vol. 16(26), pp. 21434-21445.
Ekstedt et al: "Lived Experiences of the Time Preceding Burnout": Journal of Advanced Nursing, 2005, vol. 49(1), pp. 59-67.
Sterling et al: "Allostasis: A New Paradigm to Explain Arousal Pathology";, Chapter 34 of the "Handbook of Life Stress, Cognition and Health"; S. Fisher, J. Reason (EDS); John Wiley & Sons, 1988, pp. 629-649.

* cited by examiner

STRESS-MEASURING SYSTEM

CROSS-REFERENCE TO PRIOR APPLICATIONS

This application is the U.S. National Phase application under 35 U.S.C. § 371 of International Application No. PCT/IB2013/059396, filed on Oct. 16, 2013, which claims the benefit of U.S. Provisional Patent Application No. 61/717,186, filed on Oct. 23, 2012. These applications are hereby incorporated by reference herein.

FIELD OF THE INVENTION

The present invention relates to a stress-measuring system for determining a level of stress of a user, in particular for monitoring an upcoming burnout.

BACKGROUND OF THE INVENTION

It is common knowledge that burnout is built up in a period of repeated stressors, to which the body reacts with a heightened level of physiological activity. The build-up especially occurs if this enhanced physiological activity does not get adequately restored in a subsequent period of rest or relaxation. In a review paper Bruce McEwen describes the effects of stress in health and disease (McEwen: "Central effects of stress hormones in health and disease: Understanding the protective and damaging effects of stress and stress mediators", in European J. of Pharmacology 583 (2008), p. 174-185). He describes stress as having two different sides: On the one hand, the body responds to almost any sudden, unexpected event by increasing heart rate (HR) and blood pressure (BP), helping the individual to cope with the situation; on the other hand, chronic elevation of these same parameters—e.g. chronically increased heart rate and blood pressure—produce chronic wear and tear on the cardiovascular system.

The term "allostasis" has been introduced by Sterling and Eyer to refer to the active process by which the body responds to daily events and maintains homeostasis (see "Allostasis: a new paradigm to explain arousal pathology", In Fisher, S., Reason, J. (Eds.). Handbook of Life Stress, Cognition and Health. John Wiley & Sons, New York (1988), p. 629-649). In an earlier paper McEwen introduced the terms allostatic load and allostatic overload to refer to the wear and tear that results from either too much stress or from inefficient management of allostasis, e.g. not turning off the response when it is no longer needed (Mc Ewen: "Protective and damaging effects of stress mediators", New England J. Med 338 (1998), p. 171-179).

It is clear that heart rate is a parameter that reflects this process of activation and restoration. And indeed, increased heart rate has been found to be correlated with the presence of burnout (see e.g. Boneva et al.: "Higher heart rate and reduced heart rate variability persist during sleep in chronic fatigue syndrome a population-based study", Autonomic Neuroscience: Basic and Clinical 137 (2007) 94-101).

The major restorative factor that most of us have in our lives is our vacation period. And also weekends usually have a restorative effect on our physiological activation. That is why we expect heart rate to be lower at the end of a vacation (unless it was an extreme-sports one), or at the end of the weekend. Within the period of the week, for most of us our working time slot, the major restorative factor is our night's sleep. Therefore, we also expect heart rate to have decreased gradually during the night and be at a minimum at wake-up in the morning (see van Eekelen et al.: "Circadian variation in base rate measures of cardiac autonomic activity", Eur J Appl Physiol (2004) 93: 39-46). At the end of the weekend, and at the end of the vacation, the morning heart rate might be slightly lower than is usual at wake-up during week days. But, if the process of sleep restoration is starting to become less adequate, the heart rate at wake-up (on week days as well as on weekends) will start to rise above the usual values. This is an indication that the body needs extra restorative conditions, or less stress—otherwise the consequences are a long-lasting deteriorating effect on one's health (e.g. burnout).

Burnout is a problem most of us would want to prevent, since it is not pleasurable and has significant impact on our daily behavior and activity. But also the employers would like to prevent their employees from developing a burnout, because it is bad for the overall productivity as well as for the company's image. Nevertheless, many of us do slip into it, with a prevalence as high as 5% in the Netherlands, and higher numbers estimated for Asia and the USA.

Preventing burnout is difficult, however, because many people are not inclined anymore to pay attention to their bodily signals that warn them. It is common not to notice these bodily signals, which allows us to maintain a pleasant, but unsafe, unawareness of the upcoming problems. People who have developed a burnout on the other hand usually state that afterwards they are much more capable of recognizing their body signals indicating a developing overload again.

In WO 2009/057033 A2 a system is proposed that provides a human low battery warning that indicates to the user in a very simple way that he/she should change his/her behavior by sleeping more, eating better or relaxing more to prevent the user from being over-stressed or getting a burnout. This simple warning can help people to take a break when they need it and to make sure that their "human battery" does not get empty.

One of the problems many prior art documents are focusing on is a meaningful way how to measure the vital signs (e.g. HR) of the user. If a user, for example, has to actively measure his/her HR on a daily basis, his/her consciousness might falsify the measurement, as the user's awareness is directly drawn to the measurement procedure and they might think about it or even prepare themself to it. Another problem is that users might forget to measure their vital signs, especially if this is required to be done on a daily basis. Some devices might, due to their obtrusiveness, also feel uncomfortable for the users. Since people travelling a lot for their work are exposed to many stressors and have a higher risk of developing a burnout, the mobility and practicability of such stress-measuring systems and devices is also an issue.

SUMMARY OF THE INVENTION

It is an object of the present invention to provide a stress-measuring system that enables to measure vital signs indicating the stress level of a user in a way that is as unobtrusive as possible. Furthermore, it is an object to provide a mobile solution of such a system. Preferably, the system does not require an extra action of the user in order to measure his/her vital signs.

In a first aspect of the present invention, a stress-measuring system for determining a level of stress of a user, in particular for monitoring an upcoming burnout, is presented.

The device comprises:

an alarm clock for initiating an alarm at an arbitrary preset time, wherein the system comprises an interface for switching off the alarm;

a vital sign sensor for measuring a first vital sign of the user while the user operates the interface, in particular to switch off the alarm; and a processing unit for determining the level of stress of the user based on the sensed first vital sign.

The basic idea is to use an alarm clock as platform for the vital sign/stress level measurement. Many people use an alarm clock to wake up in the morning. Even people that wake up on time without the sound of their alarm clock often use it just to be sure not to oversleep. In order to switch off the alarm of the alarm clock, users usually have to press a button or operate another kind of interface. It is exactly this action that is used according to the present invention to measure the vital sign of the user indicating the level of stress.

Since morning heart rate (especially the development of morning heart rate over a period of time) is one of the most interesting indicators for an upcoming burnout, it is ideal to use an alarm clock for measuring said morning heart rate (as the alarm clock is usually used in the morning to wake up). According to an embodiment, the vital sign sensor is therefore a heart rate sensor for measuring a heart rate of the user. However, it is to be noted that the proposed vital sign sensor may also be configured to measure other vital signs, e.g. blood pressure, body temperature, breathing rate, skin conductance, etc. All these vital signs and their development over time (over weeks and months) are indicators from which a stress level of the user may be determined in order to monitor an upcoming burnout. Even though the present invention shall not be limited to heart rate measurements, the measurement of morning heart rate shall be detailed in the following.

Normally, to stop the alarm clock, a button has to be pressed for only a fraction of a second. As also other user interactions (apart from operating a button) are generally conceivable to switch off the alarm of the alarm clock, it is herein generally referred to "an interface to switch off the alarm". The alarm can be preset by a user as this is generally known in the art. The interface can be integrated into the alarm clock, but may also be realized in any other part of the system. If the heart rate is measured while the user operates this interface, this has several advantages: First of all, this will most of the time be exactly the morning heart rate. Secondly and even more important, the user does not even recognize that the heart rate is measured, as he/she only "regularly" switches off his/her alarm clock. No extra action of the user is required. There is thus no risk for a falsification of the measurement due to active consciousness of the user. Thirdly, the integration of the stress-measuring system into an alarm clock also means an integration into an everyday technical device that most of the people use. Apart from that, an alarm clock is easy to carry on while travelling. This significantly increases the mobility and practicability of the system.

According to an embodiment, the vital signs sensor is integrated into the alarm clock, in particular into the interface of the alarm clock. While the vital sign sensor could also be realized as an external device (separate from the alarm clock), this embodiment improves the practicability and reduces the size of the system. An all-in-one device is thus realized.

One of the challenges is to measure the vital sign during the short time period while the user operates the interface to switch off the alarm of the alarm clock. Users usually operate the interface to stop the alarm for only a fraction of a second. However, it is possible to also derive the vital signal (e.g. the heart rate) from such a short interaction. Theoretically, a minimum of only two heart beats is required to measure the HR. According to an embodiment, the processing unit may be configured to extrapolate the HR from these two subsequent heart beats. In practice, the measurement of a few more heart beats may be desirable to obtain a reliable result. Therefore, the measurement of the vital sign (HR) would be improved if the user is encouraged to operate the interface for a longer period of time as usual, i.e. to press the button of the alarm clock for a bit longer time than usual.

According to an embodiment, the alarm clock is configured to switch-off the alarm only if the user keeps the interface operated for a threshold time period $\Delta t$ that is needed to measure the vital sign, otherwise to continue the alarm or to start the alarm again. $\Delta t$ is thus defined as the time period that is necessary to measure a sufficient number of heart beats in order to extrapolate the heart rate therefrom. Typically $\Delta t$ is chosen to be between three and ten seconds. $\Delta t=5$ seconds has shown to be a meaningful time period.

The procedure would then be as follows:

a) at the present time the alarm clock gives an alarm;

b) the user presses the stop button (operates the interface);

c1) if the user holds the stop button for $\Delta t$ in total, the heart rate is measured and the alarm is switched off;

c2) if the user holds the stop button for less than $\Delta t$—meaning that the time was not enough to derive the heart rate therefrom—the alarm either continues or starts again.

In this way the user is automatically encouraged to operate the interface for at least $\Delta t$. In order to improve the encouragement of the user, the system may, according to an embodiment, further comprise a guiding unit that outputs an audible, visual and/or tactile guiding signal as soon as the user operates the interface to switch off the alarm, wherein the guiding signal is configured to guide the user to keep the interface of the alarm clock operated for the threshold period of time $\Delta t$.

The guiding unit may either be a part of the processing unit or may be realized as an actuator that is connected with the processing unit. For example, this guiding unit/actuator could play music for the time period $\Delta t$. This music will remind the user to operate the interface, i.e. to keep his/her finger on the button long enough. Alternatively, a visual, tactile and/or any other audible feedback could be given to the user as soon as the vital sign measurement (HR measurement) is completed. In contrast to a "regular" alarm clock, the user only has to press the switch-off button a little longer than usual.

In any case the proposed system could, according to an embodiment, further comprise an initialization unit that initializes the vital sign sensor to measure the vital sign of the user as soon as the user operates the interface of the alarm clock. This ensures that the vital sign measurement is started right from the beginning when the user tries to switch off the alarm. The initialization unit does not have to be any extra part, but may be realized as a small sensor that senses the user's interaction.

There are several ways for measuring the heart rate in the above-mentioned way.

According to a first embodiment, the vital sign sensor is a photoplethysmography (PPG) sensor that is integrated into the interface of the alarm clock and configured to measure a heart rate at a finger tip of the user. Such PPG sensors are already known in the art. However, an integration of such a PPG sensor into an alarm clock, as proposed herein, is not known so far.

PPG sensors are usually used to measure a blood pulse wave of a person over a time to generate a heart rate signal. A PPG sensor usually includes a photodetector that measures the absorbance of the blood at different wavelengths allowing a determination of the light absorbance due to the pulsing arterial blood. A PPG sensor can be used in reflection mode or in transmission mode. Normally, a wavelength in the near-infrared is used because there the strongest modulation of the signal occurs due to light absorption in the hemoglobin in the blood. Details on the background of photoplethysmography can be found in Webster J. G.: "Medical instrumentation, application and design", Second Edition, Houghton Mifflin Company, 1992. Further information can be found in Allen J.: "Photoplethysmography and its application in clinical physiological measurement", Physiol. Meas. 28 (2007) R1-R39.

According to a further embodiment of the present invention, the vital sign sensor may alternatively be realized as an electrocardiography (ECG) sensor wherein at least one ECG electrode is integrated into the interface of the alarm clock. The HR can thus be extracted from the ECG. The ECG can be measured, for example, between the two fingers each at another hand. Therefore, two ECG electrodes may, according to an embodiment, be integrated into the interface of the alarm clock. In this embodiment the user has to touch both ECG electrodes simultaneously to switch off the alarm and to have the heart rate be measured concurrently. Alternatively, the second ECG electrode can be integrated into a bed of a user or into any other external device.

A third alternative to measure the heart rate is by using remote photoplethysmography (remote PPG). According to an embodiment of the present invention, the vital sign sensor comprises a vital signs camera using remote PPG to determine a heart rate of the user. The vital signs camera can either be integrated into the alarm clock or realized as an external device. As soon as the user operates the interface to switch off the alarm, the vital signs camera is switched on and the heart rate is extracted. Thereto, the vital signs camera is usually focused on the face of the user to measure his/her heart rate in just a few seconds. In a similar manner, the heart rate could also be measured from a hand of the user. So the vital signs camera built in the alarm clock could be configured to detect a hand and subsequently start the heart rate measurement. To comfort the user, the system could use IR instead of visible light.

Further information about remote PPG imaging can, for instance, be found in Verkruysse W.: "Remote photoplethysmographic imaging using ambient light", Optics Express, Vol. 16, No. 26, December 2008. Remote PPG is based on the principle that temporal variations in blood volume in the skin lead to variations in light absorptions by the skin. Such variations can be registered by a video camera that takes images of a skin area, e.g. the face, while processing calculates the pixel average over a manually selected region (e.g. a part of the cheek). By looking at periodic variations of this average signal, the heart beat rate and respiratory rate can be extracted.

Thus, the pulsation of arterial blood causes changes in light absorption. Those changes observed with a photodetector (or an array of photodetectors) form a PPG signal. Pulsation of the blood is caused by the beating heart, i.e. peaks in the PPG signal correspond to the individual beats of the heart. Therefore, a PPG signal is a heartbeat signal in itself. The normalized amplitude of the signal is different for different wavelengths, and for some wavelengths it is also a function of blood oxygenation.

In summary, three different (alternative) methods are envisaged within the scope of the present invention to derive the heart rate of the user while he/she switches off the alarm clock:

1. using a PPG sensor to measure the heart rate from the finger tip of the user;
2. extracting the heart rate from an ECG sensor that is integrated into the interface of the alarm clock;
3. using a vital signs camera for remote PPG, wherein the camera may either be an external device or integrated into the alarm clock as well.

According to a further embodiment of the present invention, the stress-measuring system further comprises a fingerprint sensor that is integrated into the interface of the alarm clock.

If said interface is realized as a button, the fingerprint sensor is integrated into the button (i.e. integrated into the surface of the button). This allows to distinguish between multiple users of the alarm clock. For example, in case only one single person wants his/her heart rate to be measured for a stress level measurement, the system recognizes if another person tries to switch off the alarm clock. In this case the heart rate of the other person would, for example, not be measured and stored or processed. The data of the single person would thus not be contaminated with data from others. However, a multi-user mode is also conceivable.

The processing unit of the stress-measuring system could, according to an embodiment, also be configured to distinguish between different user profiles. In case where multiple users use the alarm clock and also want their heart rate to be measured and stored or processed, the respective heart rate measurements can be combined correctly. The stress level and the risk for an upcoming burnout could then be calculated for each user separately. The processing unit is therefore configured to evaluate a chance for an upcoming burnout based on the measured vital sign for each separate user by using information delivered by the fingerprint sensor.

Independent of a single or multi-user mode, the processing unit of the stress-measuring system according to the present invention may furthermore be configured to evaluate a chance for an upcoming burnout based on a tendency of a plurality of measured first vital signs of the same user stored in a storage unit.

The stress measuring system thereto preferably comprises a storage unit for storing the measured first vital signs of the user.

The body signals (first vital signs) are thus preferably measured over a longer period of time, e.g. over the course of weeks and/or years. The system could then measure the morning heart rate in the above-mentioned way and stores at least one heart rate value for each day in the storage unit. The chance for an upcoming burnout could then be evaluated based on the tendency of the plurality of the measured values. This means that the development of the morning heart rate is analyzed in order to forecast a burnout.

Alternatively, the measured morning heart rate values could be compared each day in an absolute sense with a threshold heart rate value in order to directly warn a user if the morning heart rate value is too high in an absolute sense. In this case, the tendency does not have to be analyzed. However, both above-mentioned possibilities for analyzing the morning heart rate (tendency or absolute value) could also be combined.

According to a further embodiment, the stress-measuring system according to the present invention comprises a feedback unit for indicating a burnout status to the user in audible, visual or tactile form. According to an exemplary embodiment, a display could be integrated into the alarm clock that visualizes the burnout status in text form or by the usage of visual icons. Another possibility is that a blinking light is used to attract attention. Alternatively, the feedback unit could comprise a loudspeaker through which a spoken advice is provided to the user. This message could, for example, advise the user to go to a doctor. According to another alternative, the advice could be given in the form of a tactile feedback, e.g. the alarm clock could vibrate to give an alarm signal. The above-mentioned feedback types (audible, visual and/or tactile feedback) could also be combined.

According to a further embodiment, the feedback unit is configured to indicate the burnout status only upon request of the user.

The user may, for example, have to press a button to see the message. In this case, the user has to ask for the burnout status so that the advice is not presented to him/her without the user specifically initiating it. In a more extended embodiment, the stress-measuring system could be connected to a network (e.g. to the Internet) so that the stress-measuring system could automatically transfer the measurement data to a qualified and trusted physician for evaluation prior to (or after) a warning to the user.

According to a still further embodiment, the stress-measuring system further comprises an activity sensor that is arranged in or around a bed of the user and configured to unobtrusively measure a second vital sign of the user when the user is in bed, wherein the processing unit is adapted to determine the level of stress based on the first vital sign and/or the second vital sign.

The "second vital sign" could also be a heart rate, in particular a heart rate that is measured during sleep. In this embodiment, the morning heart rate (first vital signal) could be measured as explained above (using the alarm clock) and the heart rate during sleep (second vital sign) could be measured using the activity sensor. This activity sensor could be realized by a camera with HR detection (vital signs camera, similar as explained above) that is directed to the face of the sleeper. Alternatively, the activity sensor could comprise a pressure or piezoelectric sensor. This pressure or piezoelectric sensor could be integrated into a mattress of the user's bed. The heart rate during sleep could then be derived from the pressure variation that is measured with the pressure or piezoelectric sensor using ballistocardiography.

According to a further embodiment, the activity sensor may be furthermore configured to measure a movement of the user in bed and to derive a sleep-wake pattern therefrom, wherein the processing unit is adapted to determine the level of stress based on the first vital sign and/or the second vital sign and/or the sleep-wake pattern. In this case, the processing unit processes even more information that is included in order to derive the burnout status. The quality and preciseness of the burnout forecast is thereby significantly increased.

The activity sensor for measuring the heart rate during sleep may also be combined (in the same device) with the activity sensor for measuring the movement of the user in bed. Therefore, the number of alternating periods may be derived as a sleep fragmentation number, and the relative length of the sleep periods may be taken as a measure of the sleep-wake ratio. Both the heart rate data and the sleep data may be stored in the above-mentioned storage unit with (at least) one value each day. These values can again, as mentioned above, be compared separately to representative threshold values or a tendency over a certain period of time may be analyzed.

According to a further embodiment of the present invention, the processing unit is configured to determine a minimum of the measured second vital signs of the user during sleep (HR during sleep), wherein the processing unit is adapted to include said minimum into the determination of the stress levels/burnout forecast. The lowest heart rate during sleep (minimum heart rate) is as well a very good indicator for the overall restoration of the user (during sleep).

In practice, the processing unit could be configured to combine all the above-mentioned measurements, i.e. the morning heart rate, the sleep fragmentation, the wake-sleep ratio and the minimum heart rate during sleep, in order to calculate an overall restoration value of the user and to determine the level of stress therefrom.

Furthermore, the processing unit may be configured to include at least one of the following information into the determination of the stress level: a time information, a calendar information, in particular a calendar information if it is a week day, a weekend or a holiday, an information about a family history of the user and/or an information about a physical activity of the user. This allows to even more personalized the algorithm of the stress-level determination for the forecast of a possibly upcoming burnout. Differentiating between measurements taken on working days, weekends or holidays allows to even more precisely predict an upcoming burnout. Taking family history or additional environmental factors into account is also important to individualize the algorithm.

BRIEF DESCRIPTION OF THE DRAWINGS

These and other aspects of the invention will be apparent from and elucidated with reference to the embodiment(s) described hereinafter. In the following drawings.

DETAILED DESCRIPTION OF THE INVENTION

Figure 1:
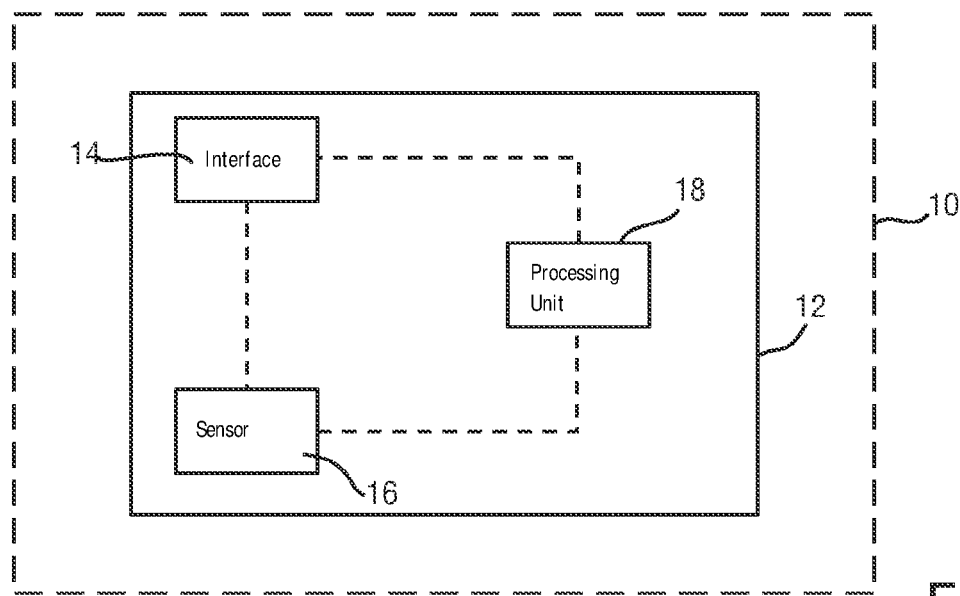
FIG. 1 shows a schematic diagram illustrating general components of a stress-measuring system according to the present invention.

FIG. 1 shows a schematic diagram illustrating the components of a stress-measuring system according to the present invention. The stress-measuring system is therein in its entirety denoted with reference numeral 10. The stress-measuring system 10 is used for determining a level of stress of a user, in particular for monitoring the risk of an upcoming burnout. As a platform for this stress-measuring system 10, an alarm clock 12 is used. Details of the alarm clock 12 will be described further below with reference to FIGS. 3 and 4.

The alarm clock 12 can be a regular alarm clock that allows to produce an alarm at an arbitrary time that may be manually or automatically set by a user. The alarm clock preferably comprises an interface 14. This interface 14 may, for example, be realized as a button with which the alarm of the alarm clock 12 can be manually switched off. Further, the stress-measuring system 10 comprises a vital sign sensor 16 and a processing unit 18.

The vital sign sensor 16 allows to measure a first vital sign of the user (e.g. a heart rate, a blood pressure, a breathing rate, a skin conductance, a body temperature etc.). Details of the vital sign sensor 16 and different embodiments how to implement the vital sign sensor 16 will also be described further below with reference to FIGS. 3 and 4.

The processing unit 18 is configured to determine the level of stress of the user based on the first vital sign that is measured with the vital sign sensor 16. The vital sign sensor 16 is preferably integrated into the alarm clock 12; so is also the processing unit 18 preferably integrated into the alarm clock 12. However, it is to be noted that the processing unit 18 may also be realized as a separate computing device (not integrated into the alarm clock 12). In this case, the processing unit 18 is preferably connected to the alarm clock 12 (also to the vital sign sensor 16 and the interface 14) either by a hard-wired connection or via a wireless connection (e.g. via a Bluetooth®, wireless Internet, or an infrared connection).

A central idea of the present invention is to couple the interface 14 for switching off the alarm of the alarm clock 12 with the vital sign sensor 16. In this way, the user's interaction with the alarm clock 12 while switching off the alarm is at the same time also used to measure the above-mentioned first vital sign of the user. The vital sign sensor 16 may, for example, be realized as a heart rate sensor that is integrated or at least electronically coupled with the interface 14 for switching off the alarm of the alarm clock 12. Thinking of a regular button (interface 14) that a user has to press to switch off the alarm clock's alarm, the vital sign sensor 16 (e.g. heart rate sensor) can, for example, be integrated into this button. Then, the vital sign (e.g. the heart rate) of the user can be measured while the user presses the button to switch off the alarm.

Since most of the people use an alarm clock 12 to wake up in the morning, this represents an ideal way to measure the heart rate right after wake-up. As it has been already elaborated in the introductory portion of the description, this wake-up heart rate is a good indicator for the stress level of the user. The wake-up heart rate is in particular an indicator that gives feedback about the restoration of the user during sleep.

One of the main benefits of the present invention is that the stress measuring system 10 allows to switch off the alarm clock 12 and measure the first vital sign (e.g. the heart rate) in one go without the need of a further user interaction. A user might therefore not even recognize that his/her heart rate is measured, as he/she "only" turns off the alarm of the alarm clock 12 in a more or less usual manner.

The main advantage is that the user does not have to wear any extra device, such as a wristband that measures the heart rate. Secondly, there is no risk of falsifying the heart rate measurement, since the user does not even recognize the heart rate measurement and can thus not psychologically prepare for it. Thirdly, the integration into an alarm clock 12 realizes a mobile solution that may also be carried on during travelling.

Figure 3A:
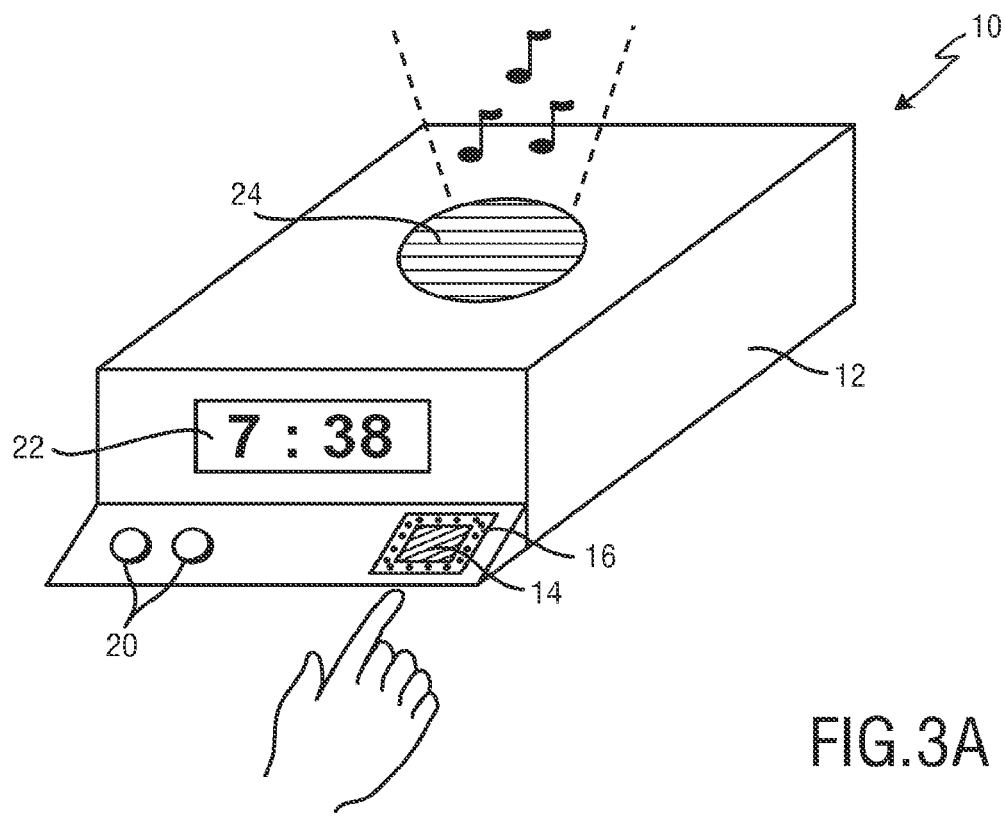
FIGS. 3A to 3C schematically illustrate three different embodiments of the stress-measuring system according to the present invention.
Figure 3B:
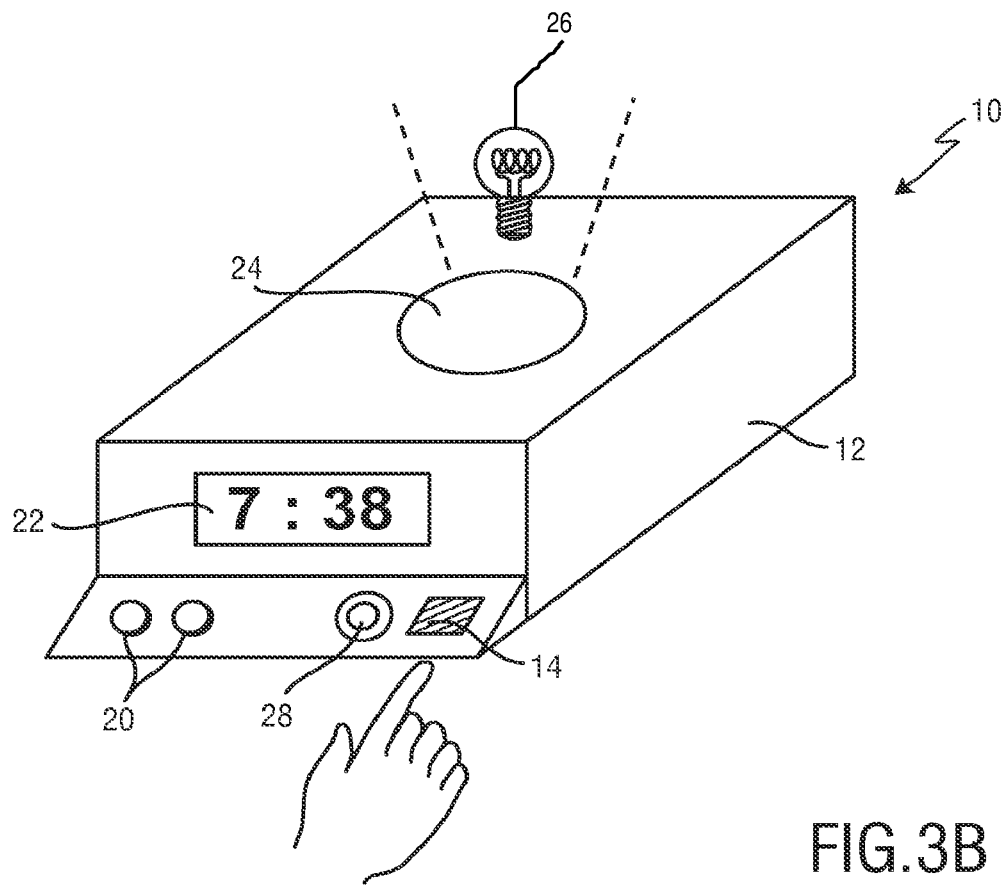
Figure 3C:
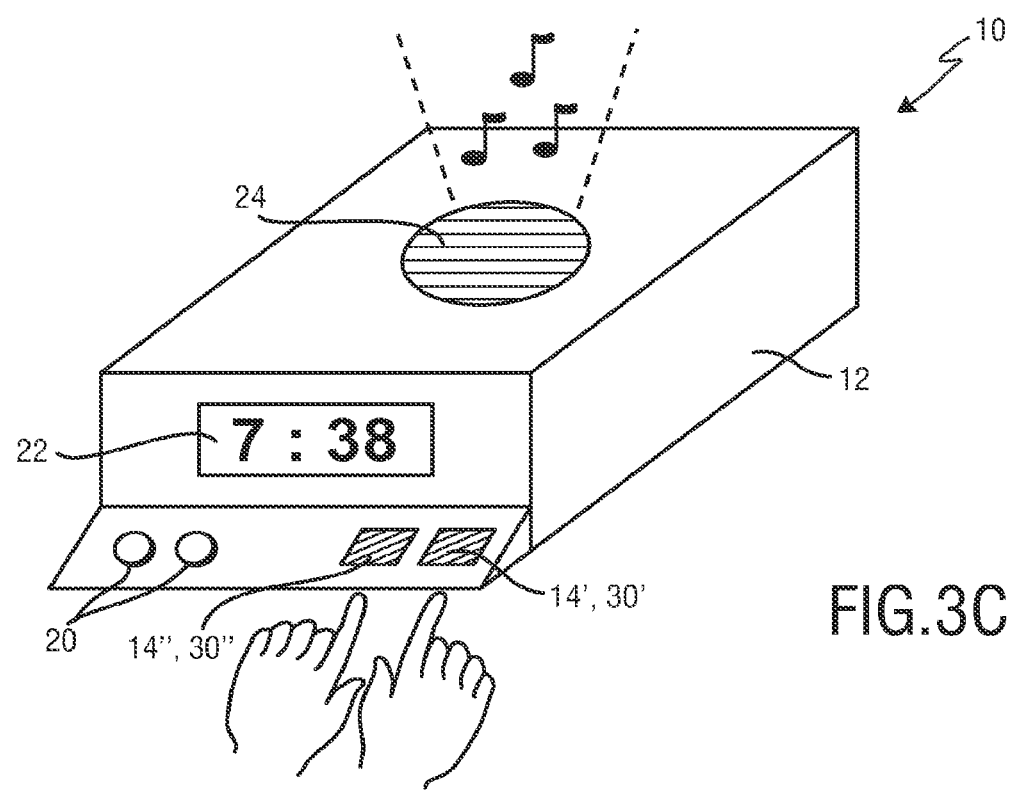

FIGS. 3A to 3C show different embodiments how the stress-measuring system 10 may be implemented in practice. Generally, a regular (digital) alarm clock 12 may be used. This alarm clock 12 should be able to produce any kind of alarm at an arbitrary time that may be set by a user. It could, for example, comprise several buttons 20 that allow to set the time of the alarm clock and/or to set the time of the alarm (wake-up time). Of course, also other functions may be integrated into a user menu of the alarm clock 12, such as the possibility to store different wake-up times, or the possibility to set the alarm only on week days, or the possibility to switch off the display 22 during the night, etc.

The alarm may be produced in many ways. Usually, a loudspeaker 24 is used to produce an alarm tone or any freely choosable melody (e.g. taken from a CD, an MP3 or directly from the radio). However, the term "alarm" shall not be restricted to any audible signal, but shall also include visual or tactile signals. Any kind of vibration of the alarm clock 12 could be also be used as an alarm to wake up the user. Similarly, as this is also schematically illustrated in FIG. 3b, a light source 26 could be used for generating an alarm signal. As this is known from many prior art alarm clocks, such a light source 26 could either produce a blinking light or a light that continuously increases the light intensity at or before the alarm time allowing a very smooth wake-up. Such a visual alarm signal shall herein also be denoted as "alarm" in general.

According to the first exemplary embodiment shown in FIG. 3A, a PPG sensor may be used as vital sign sensor 16. This PPG sensor 16 may be either integrated into the interface 14 or arranged below the interface 14. It allows to measure a heart rate at a finger tip of the user. The PPG sensor 16 may be used in either transmission or reflection mode to measure the heart rate of the user. The interface 14 to switch off the alarm of the alarm clock 12 could be realized as a regular button that has to be pressed or as a sensor array that only has to be touched (not pressed). As soon as the user operates the interface 14, the PPG sensor 16 starts to measure the heart rate of the user. In order to receive a reliable heart rate measurement, the user only has to press or touch the array 14 a little longer than usual (e.g. for several seconds, as this will be explained with reference to FIG. 4).

Another possibility to derive the heart rate during this user interaction (pressing or touching the interface 14) is schematically illustrated in FIG. 3B. According to this embodiment, the heart rate is measured using remote PPG. A camera 28, e.g. a Philips VITALSIGNS CAMERA (VITAL SIGNS CAMERA is a registered Trademark of Koninklijke Philips N. V.), can be used to determine the heart rate. Usually, this vital signs camera is focused on the face of the user as soon as he/she presses or touches the interface 14 to switch off the alarm of the alarm clock 12. In a similar manner, the heart rate can also be measured by focusing the hand of the user as soon as he/she touches the interface 14.

In both cases, the vital signs camera 28 preferably focuses a part of the skin of the user. As already mentioned above, remote PPG is based on the principle that temporal variations in blood volume in the skin lead to variations in light absorptions by the skin. Such variations can be registered by the video camera 28 that takes images of any skin area (either in the face or on the hand). By looking at these periodic variations, a signal can be derived from which the heart beat rate can be extracted. In a practical implementation, the processing unit 18 could have software stored thereon to carry out the known remote PPG algorithm. It could, for example, use the Philips vital signs app.

It is to be noted that the vital signs camera 28 does not necessarily need to be integrated into the alarm clock 12. The vital signs camera 28 could also be realized as an external device that is, for example, arranged next to the alarm clock 12 or next to the bed of the user. It may of course also be arranged on a wall next to the bed of the user. However, an integration into the alarm clock is preferable.

A third possibility of measuring the heart rate, while the user switches off the alarm of the alarm clock 12, is schematically illustrated in FIG. 3C. Instead of a PPG sensor, an electrocardiographic (ECG) sensor 30 is used in this example. As it is known from the state of the art, an ECG sensor also allows to measure the heart rate. The ECG could, for example, be measured between two fingers of the user each at another hand. Therefore, the alarm clock could comprise two interfaces 14', 14", into which two ECG electrodes 30', 30" are integrated. To turn off the alarm of the alarm clock 12, the user then has to touch both electrodes 30', 30" simultaneously. Alternatively, the alarm clock 12 could comprise only one ECG electrode 30, whereas the other electrode can, for example, be formed by the bed of the user. However, this would hamper the mobility of the system.

Independent on how the heart rate of the user is measured (either of the three above-mentioned possibilities), the processing unit 18 is configured to determine a level of stress of the user based on the measured heart rate. Several algorithms can be used therefor. The determination of the stress level of the user may be based on a single heart rate measurement. In this case, the measured heart rate is compared with a threshold value. Personal information (e.g. age, weight, gender of the user) may also be taken into account. This allows to determine a so-called stress level index. Alternatively, the determination of the stress level may also be based on several heart rate measurements. In particular for monitoring a risk of an upcoming burnout, which is one of the main targets of the present invention, the trends in the heart rate over a long-term period (over weeks, months or years) may be analyzed. This could be done by a software algorithm that is processed in the processing unit 18. Details on how to determine the risk of an upcoming burnout will be explained further below.

In case a trend in subsequent heart rate measurements is analyzed, it is preferred that the stress-measuring system 10 further includes a storage unit 32. This storage unit 32 is used to store the measured vital signs (heart rates) of the user. It could be realized as any type of memory medium, e.g. as a hard drive, that is integrated into the alarm clock 12 (see FIG. 2).

Figure 2:
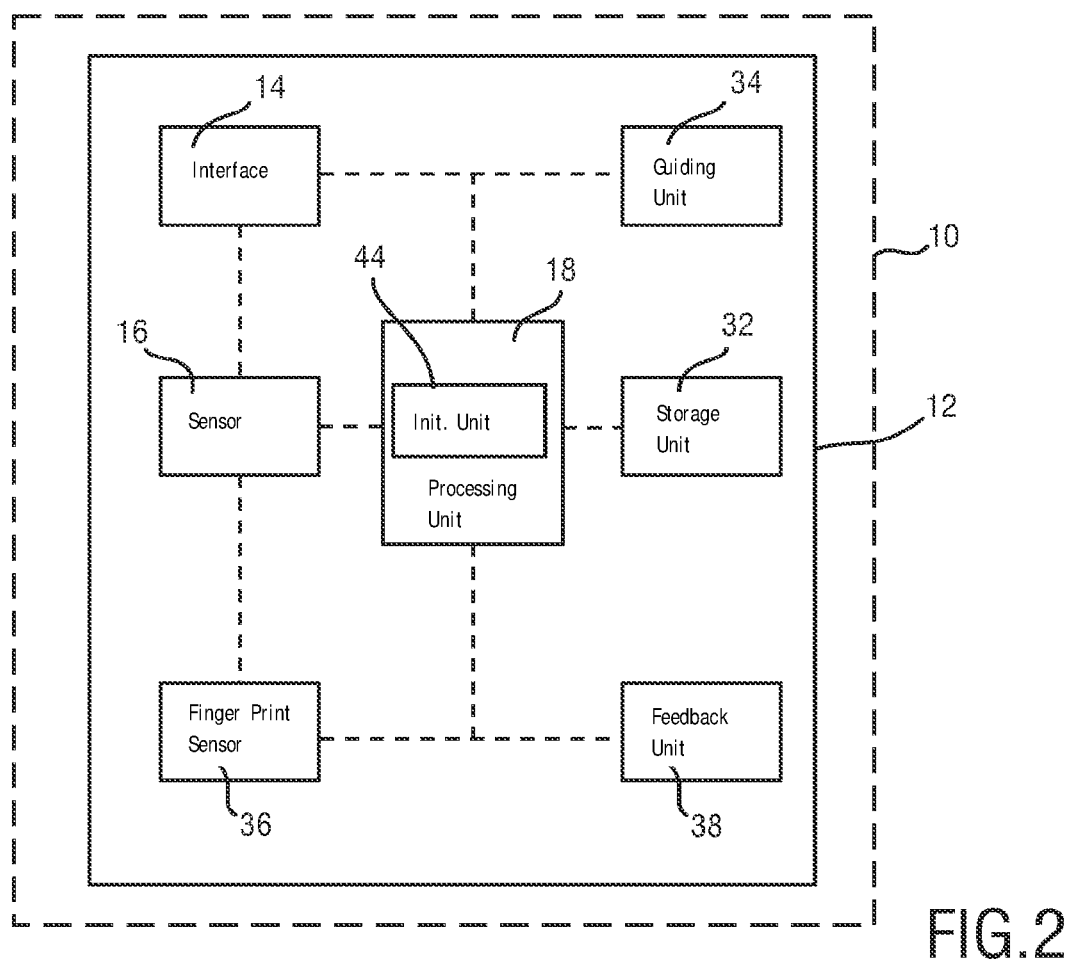
FIG. 2 shows a schematic diagram illustrating further (optional) components of the stress-measuring system according to the present invention.

FIG. 2 illustrates further (optional) components of the stress-measuring system 10. A guiding unit 34 could be provided that outputs an audible, visual and/or tactile guiding signal as soon as the user operates the interface 14 to switch off the alarm. This guiding signal can be used to guide the user to keep the interface 14 of the alarm clock 12 operated for a threshold period of time Δt. A melody or a simple tone could be produced by the guiding unit 34 starting as soon as the user operates the interface 14 (presses the button 14) and finishing as soon as the heart rate measurement is completed.

According to all of the above-mentioned ways of measuring the heart rate (PPG at fingertip, remote PPG or ECG), at least two subsequent heart beats need to be measured. Otherwise, it would not be possible to extrapolate the measured heart rate interval to receive a reliable heart rate value. The guiding unit 34 could thus encourage the user to operate the interface 14 long enough in order to be able to carry out a reliable heart rate measurement. Of course, the guiding unit 34 could also produce the guiding signal in another form (e.g., in visual or tactile form). In all cases, the guiding unit could be represented by a small actuator that is integrated into the alarm clock 12.

The alarm clock 12 may also feature a fingerprint sensor 36 that is integrated into the interface 14 of the alarm clock 12. The fingerprint sensor 36 can, for example, be added to the surface of the interface button 14 to distinguish between multiple users of the alarm clock 12. This allows to exactly identify a user. Heart rate measurements of one user will thus not be interchanged with heart rate measurements of other users. The processing unit 18 could have software stored thereon that distinguishes between the different users and stores them e.g. in separate folders within the storage unit 32.

Furthermore, the stress measuring system 10 may comprise a feedback unit 38. This feedback unit 38 may be used for indicating a burnout status to the user in audible, visual or tactile form. The feedback unit 38 may, for example, warn the user that there is a high risk for a burnout. A blinking light could appear or a spoken message could be presented to him/her. In practice the feedback unit 38 outputs its feedback either in visual form using the display 22, or in audible form using the loudspeaker 24, or in visual form using the light source 26.

Even further, the stress measuring system 10 may comprise an initialization unit 44 that initializes the vital sign sensor 16 to measure the vital sign of the user as soon as the user operates the interface 14 of the alarm clock 12. This initialization unit 44 could be software-based and integrated into the processing unit 18. It ensures that the vital sign measurement (heart rate measurement) is initialized as soon as the user operates the interface 14. It may also be realized by a movement sensor that detects the movement of a hand. In this way, the system 10 is prepared to start the process already before the user touches the interface 14 (already when he/she approaches it).

Figure 4:
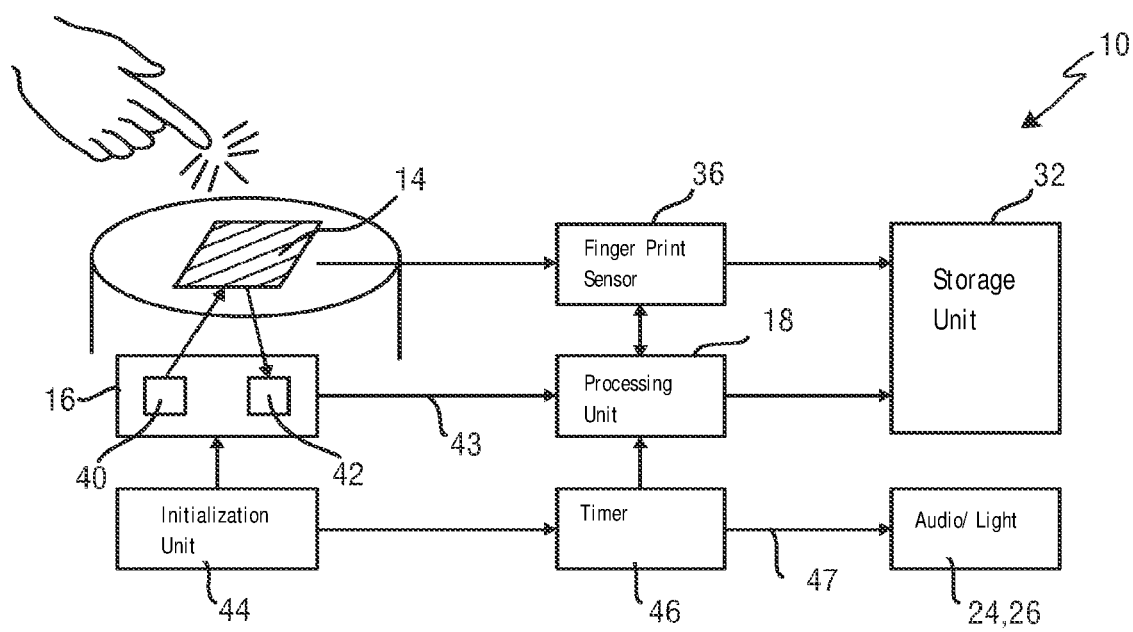
FIG. 4 shows a schematic diagram illustrating a technical principle of the stress-measuring system according to the present invention.

The whole measurement process is, in a schematic way, again realized in FIG. 4. It illustrates the measurement in case a PPG sensor is used (see first embodiment illustrated in FIG. 3A). However, the illustrated procedure may be transferred with only slight adaptations to the other two mentioned ways of measuring the heart rate (remote PPG or ECG).

First, the user touches the interface 14. The initialization unit 44 recognizes this interaction and turns the vital sign sensor 16 on. A signal is given that indicates that the interface 14 is touched/pressed. A light source represented by block 40 then emits light to the finger tip of the user. A receiver represented by block 42 receives the reflected light and transmits the received signal 43 to the processing unit 18. Concurrently, the fingerprint sensor 36 may identify the user. The heart rate is then calculated/processed by the processing unit 18 using the received heart rate signal 43. A timer 46 may be used to measure the time Δt that is needed for extracting the heart rate with the vital sign sensor 16. This time signal 47 produced by the timer 46 may be transferred to the loudspeaker 24 or light source 26. The alarm produced by the loudspeaker 24 or light source 26 is, for example, only switched off if the user keeps the interface 14 operated for the threshold time period Δt that is needed to measure the heart rate. Otherwise it continues the alarm or starts the alarm again. This process may be accompanied by the guiding signal produced by the guiding unit 34, as this has been mentioned before. Finally, the calculated heart rate and the user identity may be saved within the storage unit 32. The data could also be directly transferred (e.g. via Internet) to a doctor who could evaluate the risk for an upcoming burnout.

Figure 5:
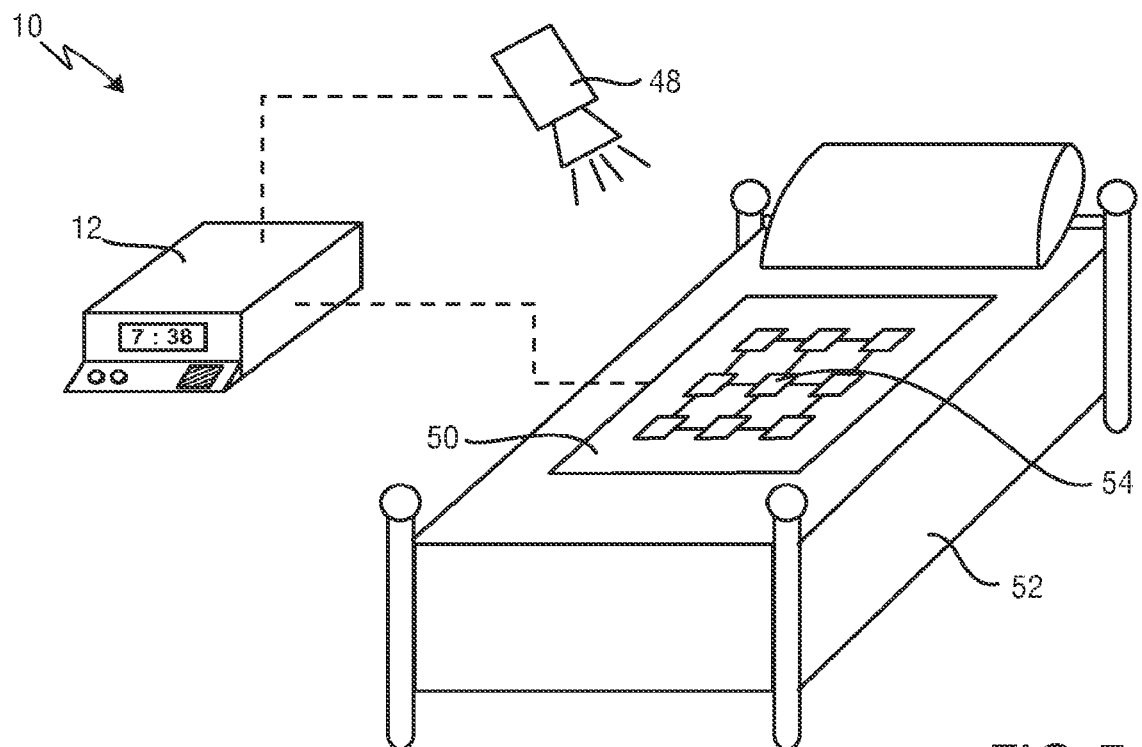
FIG. 5 schematically illustrates a further embodiment of the stress-measuring system according to the present invention.

A further embodiment of the present invention is schematically illustrated in FIG. 5. In this embodiment, the stress measuring system 10 comprises, besides the above-described alarm clock 12, furthermore one or two additional activity sensors 48, 50. These activity sensors 48, 50 are arranged in or around a bed 52 of the user and configured to unobtrusively measure a second vital sign of the user, when the user is in bed. The second vital sign may, similar as first the first vital sign, also be a heart rate of the user, but may also be a measurement signal monitoring the activity of the user during his/her sleep. The processing unit 18 is in this case adapted to determine the level of stress based on all measured signals.

In an implementation of the invention, activation sensor 48 could be realized as an (additional) vital signs camera that monitors the heart rate of the user during sleep. It may be focused on the face of the user during sleep. Alternatively or in combination, an activity sensor 50 may be linked to the bed 52 of the person. The activity sensor 50 can comprise a pressure sensor or an array of pressure sensors 54 that is attached to the bed 52, e.g. integrated into the mattress of the bed 52. It allows to derive the heart rate from the pressure patterns that may be recorded with the pressure sensor array 54. One or both activity sensors 48, 50 may continuously measure the heart rate of the person during the night, and e.g. retain the average of the last five minutes. Whenever the signal, that is produced by either of the two activity sensors 48, 50, disappears, apparently the user has left his bed and the most recent five-minute average is stored as the wake up heart rate within the storage unit 32. Also the time at which this is measured may be recorded. If the user re-enters the bed after a (short) while, the measurement procedure continuous as before, and possibly a new wake-up heart rate for that day is recorded. This way at least one wake-up heart rate is registered each day. However, it is to be noted that the wake-up heart rate may still be measured in the above-mentioned way using the alarm clock 12. The activity sensors 48, 50 may in this case be used for other vital sign measurements or for monitoring the sleeping behavior of the user. It shall be also noted that in a practical implementation the stress-measuring system 10 may comprise only one activity sensor, either camera sensor 48 or pressure sensor 50.

The activity sensor 50 including the pressure sensor array 54 may monitor the activity of the user during his/her sleep. This allows to monitor repetitive changes from normal patterns of this person, which can indicate a lack of complete restoration during the sleep phase. Periods of minimal activity (sleep) and periods of substantial activity (awake) may be derived from the signal produced by the pressure sensor array 54. Their relative lengths may be calculated by the processing unit 18. This allows to derive the number of alternating periods as a sleep fragmentation number, and the relative length of the sleep periods may be taken as a measure of a so-called sleep-wake-ratio.

All data, the heart rate data and the sleep data may be processed in the processing unit 18 to determine the stress level. For example, a stress level value may be calculated. This value may be calculated each day or as an average value per week. If these values are very high in an absolute sense (that is higher than the average of the population at large), the user may be directly warned that it might be wise to visit a doctor. Usually, however, the values will be within the spread normally encountered in the population at large, and the system 10 will not give any direct warning to the user. However, all data (heart rate data and sleep data) allow to monitor whether these data have a tendency to increase in comparison to the values measured before.

A very strong indicator for an upcoming burnout is also the minimum heart rate measured during the night. It is thus preferred that the processing unit 18 also includes said minimum into the determination of the stress level of the user. The algorithm implemented in the processing unit 18 may be personalized. The algorithm may further include at least one of the following information into the determination of the stress level: a time information, a calendar information, in particular a calendar information if it is a week day, a weekend or a holiday, an information about a family history of the user and/or an information about a physical activity of the user. Including all these information into the algorithm drastically improves the position of a burnout forecast. Differentiating between measurements on work days and on weekends gives further insight.

One possible way to calculate/forecast a risk for a burnout is to calculate an overall restoration value from the combination of the measured morning heart rate, the sleep fragmentation, the wake-sleep ratio and/or the minimum heart rate during sleep. If this restoration value is within the range of normal population during the first weeks after installation of the system 10 and does not increase consistently afterwards, the risk for a burnout is identified to be fairly low. If on the other hand the restoration value is consistently outside the regular boundaries, a message will be given to the user to warn him and to recommend him to go to a doctor.

As already mentioned above, an automated system could also transfer the data to a qualified and trusted physician for evaluation prior to (or after) a warning to the person. A further possibility that may be taken into account are environmental factors. Thereto, the system could further comprise several sensors that measure the temperature, the noise and/or the light intensity within the room. These measurements could be analyzed in relation to the heart rate and/or sleep data.

Figure 6:
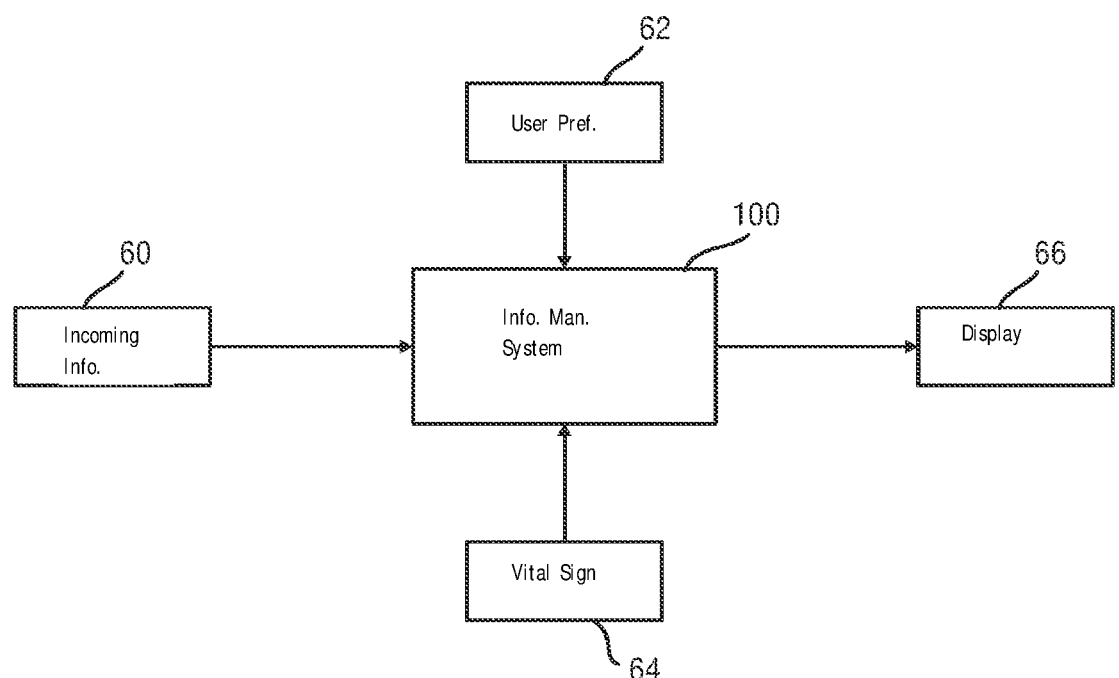
FIG. 6 shows a schematic diagram illustrating an information management system that could, according to an embodiment, be combined with the stress-measuring system according to the present invention.

The herein presented invention can be combined with an information and time management system that may be used as a burnout prevention. A schematic block diagram of such an information and time management system 100 is illustrated in FIG. 6. This information management system 100 takes users' vital signs, preferences, and history into consideration to evaluate and determine what, when, and how to present incoming data (i.e. information) to the user. It allows to selectively present data to the user and aims at reducing the psychological and physical load within a modern work environment. Consequently it contributes to the prevention or reduction of repetitive strain injuries (RSI) and burnout.

This intelligent information management system 100 (see FIG. 6) may comprise the following components: the information management system 100 organizes/manages incoming information (represented by block 60) by taking user preferences (indicated by block 62) and users' vital signs (indicated by block 64) into account and presenting the information to the user (indicated by block 66).

1. Incoming Information (60)

Incoming information (60) includes all types of digital information, such as emails, meeting requests, phone calls, text messages, Facebook notifications, news updates, etc.

2. User Preferences (62)

The user can, for example, set how, when and what information he/she wants to see. The user may also set the importance and urgency of the messages. Furthermore, the user may personalize how the smart information management system 100 operates.

3. User Vital Signs (64)

Vital signs (e.g. heart rate, sleep pattern, blood pressure, etc.) may be measured in the above-mentioned way. The information management system 100 may assess how the vital signs change in relation to the incoming and presented information. In this way, the system 100 learns how a certain type of incoming data influences the user. This learning happens automatically, as follows:

At the very beginning when the system 100 is first installed to the user's device (computer, smartphone, iPad etc.), the system passively gathers information about the user. It analyzes the incoming data and builds links to the vital signs that are measured from the user. This continues for a defined period of time, for example two months. After two months, the system is fully operational and ready to assist the user, as sufficient data have been collected and a user profile has been created. The system can now accurately predict effects of incoming information on the user. New incoming information is used to update the corresponding user profile. Learning and adaptation is done using different data mining, natural language processing and artificial intelligence tools and algorithms.

Vital signs that are measured include e.g. heart rate, heart variability, skin conductance and breathing patterns. These measurements can be easily done using Philips applications and devices such as a vitality bracelet and a vital signs camera. In addition, epidermal electronics patches can be attached to a user's body and such data can be collected at all times without the need of any devices. Taking the technological developments into account, collection and processing of the physiological data will become easily accessible and a common practice.

4. Information Management System (100)

The information management system could be implemented as a software. This software may have different data processing algorithms working in parallel. All types of data 60 coming from the devices, user preferences 62, and vital signs 64 are analyzed and a user profile or multiple user profiles may be created. Based on these, the data is presented at the time, manner, format, and content most suitable to the user's condition. In an embodiment, the information management system 100 can also communicate with other information management systems, so that the different systems may learn from each other.

5. Information Presented to the User (66)

The information is not only presented to the user. The response of the user to the presented information is preferably observed as well in order to update the management system parameters accordingly.

Two practical embodiments of such an information management system 100 shall be presented in the following:

Example 1: Electronic Calendar

In the area of the paper calendar, people and/or their assistants received a request for a new appointment and were, in principle, able to plan that new appointment at a moment that was most convenient for them. It was possible to take into account that people had to travel, had to see another person first or wanted to read a report first. Also the request to him-/herself played a role. To some people a higher priority could be given than to others.

The electronic calendar has brought many new features. To plan a multiple participant meeting using paper calendars is a difficult task. However, the electronic calendar can make a suggestion in a split second for the earliest possible time slot and many alternatives.

The electronic calendar, however, has reduced the control over time drastically. Of course, people can decline an invitation for an appointment and make a suggestion for a time that fits better for them. But this is extra work. In addition this gives a strange, negative signal to the others. By monitoring the user's response (physical signals, working patterns, speech, facial expressions, etc.) to such meetings for a specific amount of time, the information management system 100 gets a feedback about the user's personality and his/her way of responding to such situations. Then, if it is detected that having multiple adjacent meetings has undesired effects (which in long term can lead to burnout or RSI) on the person, adjacent time slots may, for example, be automatically blocked in the electronic calendar. This may also depend on, for example, the existing appointments or the content-importance of the new appointment, so that the user has enough time to prepare for a meeting, or to recover after the meeting.

Example 2: Email

In the old days, the mailman came by almost once or twice per day and you had plenty of time to work or to prepare an answer without being disturbed by new mail coming in.

Next to the many positive aspects of email, there are negative aspects as well. The most important are: they come in 24/7 and they can have a very similar turnaround time.

By analyzing the content of an email, something can be said about its relevance and stress that it may cause. In case the email contains a positive answer or message, it may reduce the stress level. Whenever a negative answer or message is contained, it can be expected that the stress level will go up. The information management system 100 therefore analyzes the emails in advance before presenting it to the user. The system 100 may be configured to delay incoming emails or not to show newly received emails at the moment they enter the inbox if it is observed that receiving multiple emails can have undesired effects on the user. The mail signal may be made dependent on the time of the day. New mails may only be shown at discrete moments during the day. The mail signal may also be made dependent on the work with the computer. When working intensively, reading or typing, incoming mails may be suppressed. The mail signal may also be made dependent on the content or the sender of the incoming mail. Urgent mails or mails classified as important may of course be an exception.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A stress-measuring system for forecasting a burnout condition of a user comprising:
    an alarm clock configured to:
        generate an alarm at a preset time;
    an interface, in communication with the alarm clock, said interface configured to switch off an alarm signal generated by the alarm clock;
    a first vital sign sensor configured to measure a first vital sign of the user while the user operates the interface;
    a second vital sign sensor configured to measure a second vital sign of the user obtained during a sleep period; and
    a processor configured to:
    receive measurements associated with the first vital sign;
    determine whether a period of time the interface is operated is greater than a threshold time ($\Delta t$);
    cancel generation of the alarm after the period of time the interface is operated exceeds the threshold time;
    determine an overall restoration value from a combination of at least two of a sleep fragmentation condition, a wake-sleep ratio and a minimum heart rate during a sleep condition; and
    forecast a burnout condition based on the overall restoration value and a tendency of the overall restoration value to not increase over time.

2. The stress-measuring system according to claim 1, further comprising:
    a guiding unit configured to output at least one of: an audible, a visual and a tactile guiding signal upon operation of the interface, wherein the guiding signal is configured to guide the user to operate the interface for the threshold time ($\Delta t$).

3. The stress-measuring system according to claim 1, wherein the first vital sign sensor comprises:
    a PPG sensor integrated into the interface, said PPG sensor configured to measure a heart rate at a fingertip of the user.

4. The stress-measuring system according to claim 1, wherein the first vital sign sensor comprises:
    a camera using remote PPG to determine a heart rate of the user.

5. The stress-measuring system according to claim 1, wherein the first vital sign sensor comprises:
    an ECG sensor, wherein at least one ECG electrode is integrated into the interface of the alarm clock.

6. The stress-measuring system according to claim 1, further comprising:
    a fingerprint sensor integrated into the interface.

7. The stress-measuring system according to claim 1, further comprising:
    a storage unit for storing the measured first vital signs.

8. The stress-measuring system according to claim 1, further comprising:
    a feedback unit configured to:
        indicate the burnout status in at least one of: an audible, a visual and a tactile form, and
        provide said indication to the user upon request of the user.

9. The stress-measuring system according to claim 1, wherein the second vital sign sensor is arranged in or around a bed of the user.

10. The stress-measuring system according to claim 9, wherein the second vital sign sensor is furthermore configured to:
    measure a movement of the user;
    derive a sleep-wake pattern as the second vital sign from the measured movement.

11. The stress-measuring system according to claim 9, wherein the second vital sign sensor comprises:
    at least one of: a pressure sensor and a piezoelectric sensor.

12. The stress-measuring system according to claim 9, wherein the processor is configured to:
    determine a minimum of the measured second vital sign of the user during a sleep period.

13. The stress-measuring system according to claim 1, wherein the processor is further configured to:
    include at least one of the following information into the determination of the stress level: a time information, a calendar information, an information about a family history of the user and an information about a physical activity of the user.

14. The stress-measuring system of claim 13, wherein the calendar information is one of: a weekday, a weekend and a holiday.

15. The stress-measuring system of claim 1, further comprising:
    continue generation of the alarm when the interface has been operated for a period less than the threshold time period.

16. The stress-measuring system of claim 1, wherein the processor is further configured to:
    determine whether the overall restoration value is consistently outside a boundary associated with a normal population; and
    generate an alert when the overall restoration value is consistently outside said boundary.

* * * * *